United States Patent
Honma et al.

(10) Patent No.: US 6,867,315 B2
(45) Date of Patent: Mar. 15, 2005

(54) PREPARATION OF HIGH PURITY ALKYL GALLIUM

(75) Inventors: Takayuki Honma, Niigata-ken (JP); Takanobu Tsudera, Niigata-ken (JP); Hiromi Nishiwaki, Niigata-ken (JP); Shuji Tanaka, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/868,759

(22) Filed: Jun. 17, 2004

(65) Prior Publication Data

US 2004/0260106 A1 Dec. 23, 2004

(30) Foreign Application Priority Data

Jun. 19, 2003 (JP) .......................................... 2003-174391

(51) Int. Cl.⁷ .................................................. C07F 5/00
(52) U.S. Cl. ............................................................ 556/1
(58) Field of Search ............................................... 556/1

(56) References Cited

U.S. PATENT DOCUMENTS 3,318,931 A * 5/1967 Dotzer et al. .................. 556/1
4,604,473 A * 8/1986 Cole-Hamilton et al. ...... 556/1
6,495,707 B1 12/2002 Leese et al. .................... 556/1

FOREIGN PATENT DOCUMENTS

JP 2002-533348 A 10/2002

OTHER PUBLICATIONS

John J. Eisch, "Organometallic Compounds of Group III. I. The Preparation of Gallium and Indium Alkyls from Organoaluminum Compounds". Journal of the American Chemical Society; Oct. 17, 1962; 84(19); pp. 3605–3610.

* cited by examiner

Primary Examiner—Porfirio Nazario-Gonzalez
(74) Attorney, Agent, or Firm—Birch, Stewart, Kolasch & Birch, LLP

(57) ABSTRACT

Trialkylgallium is prepared by reacting a gallium halide or alkyl gallium with trialkylaluminum in a solvent having a boiling point which is at least 10° C. higher than the boiling point of the trialkylgallium, such as mesitylene or o-dichlorobenzene. High purity alkyl gallium is obtained in high yields.

1 Claim, No Drawings

PREPARATION OF HIGH PURITY ALKYL GALLIUM

This Non-provisional application claims priority under 35 on Patent Application No(s). 2003-174391 filed in Japan on Jun. 19, 2003, the entire contents of which are hereby incorporated by reference.

TECHNICAL FIELD

This invention relates to a method for preparing alkyl gallium compounds useful in the manufacture of compound semiconductor materials.

BACKGROUND ART

Compound semiconductor materials such as gallium arsenide, indium phosphide, gallium phosphide and mercury cadmium telluride are well known in the electronics industry as finding use in microwave oscillators, semiconductor light-emitting diodes, lasers, IR sensors or the like. In the prior art, these materials are generally prepared by a vapor phase epitaxial (VPE) method of forming at least one active layer on a crystalline substrate. It is known from the past that a compound semiconductor represented by the formula: MQ wherein M is a Group III element and Q is a Group V element can be prepared by the VPE method of reacting a trialkyl compound of element M with a gaseous compound, typically hydride of element Q.

The VPE method is advantageous in the manufacture of gallium arsenide from $Ga(CH_3)_3$ and $AsH_3$, for example. Thus, organometallic compounds, especially trialkyl compounds of Group III elements such as trimethylgallium and trimethylindium become of greater interest for the manufacture of semiconductor materials.

The quality of a compound semiconductor obtained by epitaxial growth of an organometallic compound largely depends on the purity of the starting organometallic compound. This is because impurities in the organometallic compound have substantial negative impact on the electrical and optical characteristics of the semiconductor.

In the preparation of organometallic compounds, on the other hand, organic solvents, typically hydrocarbon compounds are used solely for uniform reaction to take place. However, during the reaction, the solvent can be partially decomposed. Among decomposed products, hydrocarbon fragments having a boiling point close to that of the organometallic compound (referred to as "close boiling hydrocarbons") are entrained on the organometallic compound.

While the current industry demands high purity organometallic compounds, the inclusion of such decomposition products, especially close boiling hydrocarbons necessitates a subsequent purifying step that imposes an extra cost. Sometimes, their separation is difficult.

The close boiling hydrocarbons which cannot be removed from the organometallic compound are regarded quite harmful because they can produce carbon inclusions in any films which are formed from the organometallic compound.

It is known in the art to use a gallium halide and an alkyl aluminum compound as reactants in the preparation of an alkyl gallium compound. See J. Am. Chem. Soc., 84, 3606 (1962). The solvents used in such reaction include saturated hydrocarbons such as pentane, hexane, heptane, octane, nonane, decane and hexadecane, aromatics such as benzene, toluene and xylene (see JP-A 2002-533348), and kerosine, gasoline, and liquid paraffin. The use of these solvents, however, prevents the recovery of high purity alkyl gallium because hydrocarbons produced by side reaction, especially hydrocarbons of 5 to 8 carbon atoms, and benzene are difficult to separate when the alkyl gallium is recovered by distillation.

SUMMARY OF THE INVENTION

An object of the invention is to provide a method for preparing a high purity alkyl gallium which is free of hydrocarbon impurities originating from the solvent used for reaction.

It has been found that in the preparation of an alkyl gallium using a gallium halide and an alkyl aluminum, the use of a specific solvent ensures that a high purity alkyl gallium which is free of hydrocarbon impurities originating from the solvent is easily prepared in high yields.

Accordingly, the present invention provides a method for preparing an alkyl gallium comprising the step of reacting a compound of the general formula (1):

$$R^1_{3-m}GaX_{m-3} \qquad (1)$$

wherein $R^1$ is a monovalent hydrocarbon radical, X is a halogen atom, and m is an integer of 0 to 3, with a compound of the general formula (2):

$$R^2_3Al \qquad (2)$$

wherein $R^2$ is an alkyl radical of one or two carbon atoms, to form an alkyl gallium of the general formula (3):

$$GaR^2_3 \qquad (3)$$

wherein $R^2$ is as defined above. In the reaction, a compound having a boiling point which is at least 10° C. higher than the boiling point of the organometallic compound (or alkyl gallium) of formula (3) and represented by the general formula (4) is used as a solvent.

$$R^3_nAr \qquad (4)$$

Herein $R^3$ is independently at each occurrence hydrogen, methyl, a substituted or unsubstituted aromatic hydrocarbon radical having 6 to 16 carbon atoms or an electrophilic substituent radical, Ar is a substituted or unsubstituted aromatic hydrocarbon radical having 6 to 16 carbon atoms, and n is an integer of 1 to 14, with the proviso that n is an integer of 2 to 6 when all $R^3$ radicals are methyl.

DESCRIPTION OF THE PREFERRED EMBODIMENT

Briefly stated, the method for preparing an alkyl gallium of formula (3) according to the invention involves reaction of a compound of formula (1) with a compound of formula (2) in a solvent having a boiling point which is at least 10° C. higher than the boiling point of the alkyl gallium of formula (3).

$$R^1_{3-m}GaX_{m-3} \qquad (1)$$

$$R^2_3Al \qquad (2)$$

$$GaR^2_3 \qquad (3)$$

In formula (1), $R^1$ is a monovalent hydrocarbon radical, preferably having 1 to 8 carbon atoms, such as methyl, ethyl, n-propyl, isopropyl, n-butyl or isobutyl. X is a halogen atom, such as chloro or bromo. The letter m is an integer of 0 to 3.

Examples of the compound of formula (1) include gallium chloride, monomethyldichlorogallium, dimethylchlorogallium, triethylgallium, tri-n-propylgallium, triisopropylgallium, tri-n-butylgallium, and triisobutylgallium.

In formula (2), $R^2$ is an alkyl radical of one or two carbon atoms, specifically methyl or ethyl. Exemplary of the compound of formula (2) are trimethylaluminum and triethylaluminum.

In formula (3), $R^2$ is as defined above. Exemplary of the compound of formula (3) are trimethylgallium and triethylgallium.

The solvent having a boiling point which is at least 10° C. higher than the boiling point of the alkyl gallium of formula (3) is a compound of the general formula (4).

$$R^3{}_n Ar \qquad (4)$$

Herein $R^3$ which may be the same or different is hydrogen, methyl, a substituted or unsubstituted aromatic hydrocarbon radical having 6 to 16 carbon atoms, preferably 6 to 10 carbon atoms or an electrophilic substituent radical. Ar is a substituted or unsubstituted aromatic hydrocarbon radical having 6 to 16 carbon atoms. The letter n is an integer of 1 to 14, with the proviso that n is an integer of 2 to 6 when all $R^3$ radicals are methyl.

More illustratively, $R^3$ stands for methyl, aryl radicals such as phenyl, tolyl, xylyl, naphthyl and biphenyl, aralkyl radicals such as benzyl, electrophilic substituent radicals such as fluoro, chloro, bromo, nitro, cyano, acetyl, alkylamino, acetamide and alkoxy, and substituted forms of the foregoing radicals in which some or all of the hydrogen atoms are substituted with halogen atoms (such as chloro, fluoro or bromo), cyano, amino, alkylamino, nitro, acetoxy, acyloxy, amide, acetamide, and organoxy (such as alkoxy, alkenyloxy, and aryloxy). The letter n is an integer of 1 to 14, preferably 1 to 6. Ar stands for benzene, naphthalene, anthracene, pyrene and biphenyl, and substituted forms of the foregoing radicals in which some or all of the hydrogen atoms are substituted with halogen atoms (such as chloro, fluoro or bromo), cyano, amino, alkylamino, nitro, acetoxy, acyloxy, amide, acetamide, and organoxy (such as alkoxy, alkenyloxy, and aryloxy).

Illustrative, non-limiting examples of the compound of formula (4) include xylene, mesitylene, tetramethylbenzene, dimethylnaphthalene, trimethylnaphthalene, dimethylanthracene, phenyltoluene, phenylnaphthalene, phenylanthracene, chlorobenzene, dichlorobenzene, trichlorobenzene, chloronaphthalene, dichloronaphthalene, fluorobenzene, difluorobenzene, trifluorobenzene, hexafluorobenzene, benzotrifluoride, perfluoronaphthalene, bromobenzene, dibromobenzene, tribromobenzene, nitrobenzene, benzonitrile, acetylbenzene, acetylnaphthalene, acetylanthracene, dimethylaminobenzene, aniline, and methoxynaphthalene. Of these, preferred are xylene, mesitylene, methylnaphthalene, chlorobenzene, dichlorobenzene, chlorotoluene, fluorobenzene, benzotrifluoride, and phenyltoluene.

Preferably the solvent is used in the reaction after drying. The solvent may be removed of water by azeotroping off water, using a desiccant, or reducing the pressure below the vapor pressure of water for vaporizing off water. Exemplary desiccants include anhydrous inorganic salts such as anhydrous magnesium sulfate, anhydrous sodium sulfate, and anhydrous calcium chloride, carbodiimides such as N,N'-dicyclohexylcarbodiimide, silica gel, and molecular sieves.

When the compound of formula (1) is reacted with the compound of formula (2), the molar ratio of compound (2) to compound (1) is preferably between 3/1 and 6/1. The preferred amount of the solvent used is such that the weight ratio of the solvent to compound (1) is between 0.5/1 and 10/1, more preferably between 1/1 and 4/1.

It is recommended that pretreatment be carried out in an atmosphere from which air and water has been essentially removed, typically a purified argon atmosphere. The reaction is typically carried out in a vessel while stirring the contents. The reaction temperature is preferably in a range of 0 to 250° C., more preferably room temperature to 200° C. The reaction may be carried out under a reduced pressure, atmospheric pressure or an added pressure (up to 0.2 MPa).

The recovery of alkyl gallium from the reaction product is simply achieved by conventional distillation. Depending on the type of reactants, the product alkyl gallium and the aluminum compound may have approximate boiling points. In such a case, the product can be purified to a high purity by distillation using a precise distillation column.

EXAMPLE

Examples of the invention are given below by way of illustration and not by way of limitation.

Example 1

A 500-ml stainless steel reactor equipped with a condenser, stirrer and thermometer was thoroughly purged with helium. It was then charged with 50 g (0.28 mol) of gallium chloride and 125 ml of mesitylene, to which 68 g (0.94 mol) of trimethylaluminum was added dropwise from a dropping funnel. The reaction solution was heated at 80° C. for 2 hours and further heated until 29 g (0.25 mol) of trimethylgallium was distilled out. This corresponds to 90% of the theory. To determine the post-synthesis purity, the trimethylgallium in the double tube was analyzed for NMR spectrum by means of an NMR analyzer GSX-270 (JEOL Ltd.). The quantity of hydrocarbon impurities originating from decomposition of the solvent was below the detection limit (below 10 ppm).

Example 2

Trimethylgallium was synthesized by the same procedure as Example 1 except that o-dichlorobenzene was used instead of mesitylene. The product was analyzed for NMR spectrum, finding that the quantity of hydrocarbon impurities originating from decomposition of the solvent was below the detection limit (below 10 ppm).

Comparative Example 1

Trimethylgallium was synthesized by the same procedure as Example 1 except that toluene was used instead of mesitylene. The product was analyzed for NMR spectrum. Benzene was detected (6,900 ppm).

Comparative Example 2

Trimethylgallium was synthesized by the same procedure as Example 1 except that tetralin was used instead of mesitylene. The product was analyzed for NMR spectrum. Aromatic impurities including benzene were detected (4,200 ppm).

Comparative Example 3

Trimethylgallium was synthesized by the same procedure as Example 1 except that diisobutylnaphthalene was used instead of mesitylene. The product was analyzed for NMR spectrum. Hexane and naphthalene were detected (1,000 ppm).

Comparative Example 4

Trimethylgallium was synthesized by the same procedure as Example 1 except that tetradecane was used instead of mesitylene. The product was analyzed for NMR spectrum. Aromatic impurities including benzene were detected (5,500 ppm).

Comparative Example 5

Trimethylgallium was synthesized by the same procedure as Example 1 except that liquid paraffin was used instead of mesitylene. The product was analyzed for NMR spectrum. Hydrocarbon impurities of 5 to 8 carbon atoms were detected (3,500 ppm).

The method of the invention has the industrial benefit that alkyl gallium is prepared from alkyl aluminum as a reactant and in high yields, which is highly pure in that it is free of hydrocarbon impurities originating the solvent. Through epitaxial growth of a product containing a substantial proportion of pure organometallic compound, a semiconductor having high performance can be prepared.

Japanese Patent Application No. 2003-174391 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for preparing an alkyl gallium comprising the step of reacting a compound of the general formula (1):

$$R^1_{3-m}GaX_{m-3} \tag{1}$$

wherein $R^1$ is a monovalent hydrocarbon radical, X is a halogen atom, and m is an integer of 0 to 3, with a compound of the general formula (2):

$$R^2_3Al \tag{2}$$

wherein $R^2$ is an alkyl radical of one or two carbon atoms, to form an alkyl gallium of the general formula (3):

$$GaR^2_3 \tag{3}$$

wherein $R^2$ is as defined above, characterized by the use as a solvent of a compound having a boiling point which is at least 10° C. higher than the boiling point of the alkyl gallium of formula (3) and represented by the general formula (4):

$$R^3_n Ar \tag{4}$$

wherein $R^3$ is independently at each occurrence hydrogen, methyl, a substituted or unsubstituted aromatic hydrocarbon radical having 6 to 16 carbon atoms or an electrophilic substituent radical, Ar is a substituted or unsubstituted aromatic hydrocarbon radical having 6 to 16 carbon atoms, and n is an integer of 1 to 14, with the proviso that n is an integer of 2 to 6 when all $R^3$ radicals are methyl.

* * * * *